United States Patent [19]

Hylarides et al.

[11] Patent Number: 4,584,137
[45] Date of Patent: Apr. 22, 1986

[54] SYNTHESIS OF 1-HALOESTRADIOLS

[75] Inventors: Mark D. Hylarides; Fred A. Mettler, Jr., both of Albuquerque, N. Mex.

[73] Assignee: University of New Mexico, Albuquerque, N. Mex.

[21] Appl. No.: 597,930

[22] Filed: Apr. 9, 1984

[51] Int. Cl.⁴ .............................................. C07J 1/00
[52] U.S. Cl. .................................................. 260/397.5
[58] Field of Search ...................................... 260/397.5

[56] References Cited

U.S. PATENT DOCUMENTS 3,264,330  8/1966  Moersch et al. ................. 260/397.4
3,371,087  2/1968  Beard .............................. 260/397.4
4,340,602  7/1982  Brooks ............................. 424/243

OTHER PUBLICATIONS

Hylarides et al., "Steroids", Feb. 1984, vol. 43, No. 2, pp. 219–224.

Hylarides et al, Jour. Org. Chem. (1984) vol. 49 (15) pp. 2744–2745.

G. W. Moersch et al, "The Syntheses and Myotrophic Activity of 1-Halo-4-Methylestra-1,3,5(10)-Trienes", May 21, 1964, pp. 741–748, vol. 7.

Primary Examiner—Elbert L. Roberts
Attorney, Agent, or Firm—Charles W. Fallow; Jean A. Buttmi

[57] ABSTRACT

Estrogens characterized by an aromatic ring of the formula

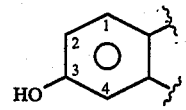

are halogenated by electrophilic substitution of a halo atom at the 1-position of the aromatic ring after protection of the sensitive 3-hydroxyl substituent and amination at the 4-position. Preferred starting materials include estrones or derivatives thereof. The estrones are preferably reduced after masking and amination to form the corresponding estradiols, which are then halogenated, deaminated and deprotected to provide the novel 1-haloestradiols.

25 Claims, No Drawings

SYNTHESIS OF 1-HALOESTRADIOLS

BACKGROUND OF THE INVENTION

The use of radiolabelled steroids for in vivo receptor binding assays is well known; generally, the efficacy of particular radiolabelled steroids is evaluated in competitive binding assays employing non-radioactive analogue as competitor. The radiolabelled steroid, to be of use in nuclear medicine applications, should exhibit a high specific activity, good chemical stability, and a high in vivo receptor binding affinity.

Since stability is essential, halogenation of the aromatic ring of native steroids has been proposed, as it is known that steroids in which the aromatic ring of the steroid nucleus is halo-substituted are generally more stable than the same steroids wherein an aliphatic carbon is halo-substituted. In some instances, however, stabilization of steroids by halogenation or radiohalogenation has significantly reduced the biological activity of the steroid so that the derivative is useless as a practical matter in applications requiring a high in vivo binding affinity between the receptor and stabilized compound. For example, estradiol brominated in the 4-position with $^{77}$Br has a high specific activity, and good chemical stability; receptor binding studies, however, indicate that 4-$^{77}$Br-estradiol has a low in vivo binding affinity for estrogen receptors, probably owing to the close proximity of the halo and hydroxyl substituents on the 3-phenol aromatic ring.

It is thus accordingly proposed to halogenate estrogens in the 1-position to stabilize the compounds while lessening the halo/hydroxyl interaction on the aromatic ring, thereby preserving biological activity of the native estrogen. The present process avoids known synthesis difficulties which have previously precluded preparation of comparable 1-haloestrogens, particularly the fact that, while the 2- and 4-positions of the phenol are highly active, the 1-position is meta to the hydroxy group, and is consequently deactivated; preferential direct electrophilic substitution at the 1-position of the aromatic ring is thus highly improbable.

SUMMARY OF THE INVENTION

The invention comprises a method for the halogenation and reduction of estrones of the formula I, or derivatives thereof:

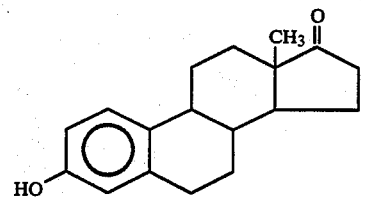

to form corresponding novel 1-haloestradiols of the formula VI:

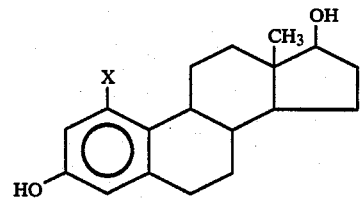

wherein X is a halogen atom, or a radioisotope thereof.

The synthesis can be completed in a short period of time, usually under about two hours, which accomodates the use of radiohalogens, which have characteristically short half lives. Further, the synthesis minimizes extensive work-up procedures between steps, which reduces handling of radioisotopes and consequent exposure to radioactivity.

DETAILED DESCRIPTION OF THE INVENTION

According to the process of the invention, direct electrophilic halogenation of the estrone aromatic ring is preceded by a series of steps which function to: (a) mask the sensitive 3-hydroxy group on the estrone starting material; (b) place an amino substituent at the 4-position of the aromatic ring to direct the subsequent halo reactant to the 1-position; and (c) reduce the cyclopentanone moiety to the corresponding alcohol moiety, according to the following reaction scheme:

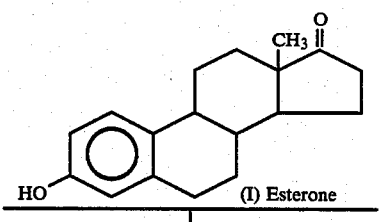

(a) Masking
Ex: Etherification
Z is a suitable masking group, e.g.,
C$_1$—C$_4$— alkyl

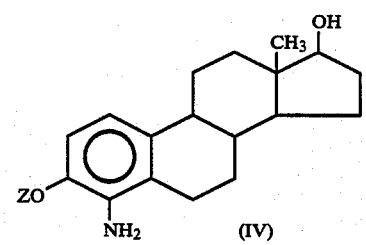

(d) Halogenation
Ex: NaBr/NCS

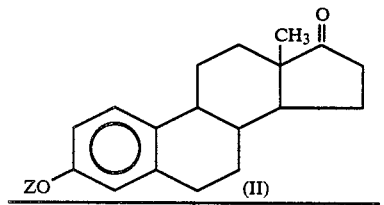

(II)

(b) Amination
Ex: Nitration,
Reduction (c) Reduction
Ex: LiAl(OtBu)₃H

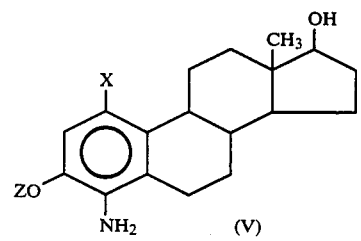

(V)

(e) Deamination
Unmasking
Ex: (1) HONO
(2) BBr₃

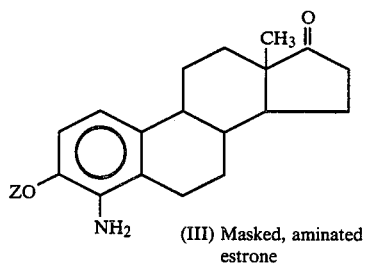

(III) Masked, aminated estrone

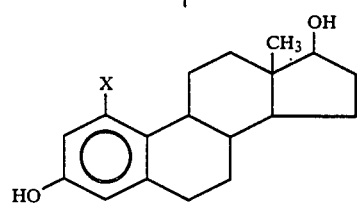

(VI) 1-Haloestradiol

The starting estrone is readily commercially available. In addition to the simple estradiol derivatives of the Formula IV, substituted estradiols comprising derivatives of compounds of the Formula IV are useful, such as compounds of the Formula IVa:

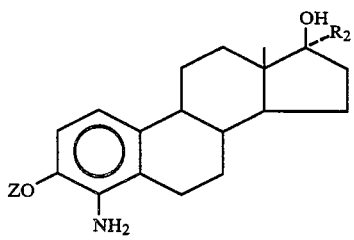

IVa wherein Z is alkyl, especially $C_1$–$C_4$-alkyl, and $R_2$ is alkyl, alkenyl, or alkynyl, especially ethynyl. These compounds, and similar R-substituted 4-amino masked estradiols are prepared in known fashion from the starting estrone.

The masking group is adapted to protect the phenolic hydroxyl during the course of the reaction, and must comprise a group which is stable during the subsequent amination, which permits halogenation, and which is removable to provide the desired estradiol at the end of the reaction. Compounds of the Formula II wherein Z is methyl, i.e., 4-aminoestrone-3-methylether, appear to be particularly suitable, whereas tetrahydropyranyl and methoxyethoxy methyl ethers appear to be unsuitable phenolic protecting groups, as while bromination was successful, deamination could not be completed.

As a practical matter, masking (step a) and amination (step b) are conducted together in known manner, as by nitration, etherification and reduction of the nitro group, as reported by Utne, et al, *J. Org. Chem.* 33:2469–72 (1968), incorporated herein by reference. In this subprocess, the estrone is first nitrated to place nitro groups on the 4-position of the estrone; the masking group, in this instance a methyl ether, is then added by etherification, and the nitro group reduced to give a masked, aminated compound of the Formula III, such as 4-aminoestrone-3-alkylether. This compound is then reduced and halogenated according to the present invention to give an intermediate capable of being unmasked and deaminated to the desired 1-haloestradiols. It is noted that the amination procedure, or a similar procedure which substitutes a group on the 4-position of the aromatic ring (a) which is capable of directing the subsequent halo substituent to the 1-position, and (b) which can readily be subsequently removed, is essential to the process of the invention. In the present exemplified process, it is noted that nitration of the starting estrone will place nitro groups in the 2- and 4-position on the estrone A-ring; the 4-substituted estrones are separated from the 2-substituted estrones prior to etherification to minimize the presence of 2-nitroestrone and consequently 2-aminoestrone.

The masked, aminated compound of the Formula III is then reduced in step (c) to compounds of the Formula IV, wherein masked 4-aminoestrone is reduced to masked 4-aminoestradiol. The preferred reducing agent is LiAl(OtBu)₃H, lithium aluminum tri-tert-butoxyhydride, as this agent is stereoselective for the desired 17β-alcohol, and thus minimizes contamination with the 17α-alcohol epimer. If some contamination can be tolerated, however, a variety of known reducing agents which will reduce the keto group on the cyclopentanone moiety to the corresponding -OH group, while leaving the rest of the molecule undisturbed, will be useful. Such agents include, for example, LiAlH₄ and NaBH₄. Useful solvents are known, particularly including tetrahydrofuran (THF).

The masked 4-aminoestradiol of the Formula IV, or suitable derivatives thereof, is then halogenated with an electrophilic halogenating species which will effect electrophilic aromatic substitution in the 1-position thereof. Halogenation with all halogen species, including fluorine, chlorine, bromine, and iodine, and radioisotopes thereof, especially $^{77}Br$ and $^{82}Br$ are contemplated, with the exception of those species sterically hindered in the 1-position (iodo may be particularly susceptible). Suitable halogenating species include halide salts, especially alkali metal and ammonium salts, in conjunction with species known to promote the electrophilic character of the halogen atom; as is well known in the art, N-chlorosuccinimide (NCS) is a particularly suitable promotor. The use of reaction systems comprising NaX/NCS or NH4X/NCS, in a solvent system such as dioxane-acetic acid which permits a "one-pot" halogenation and deamination reaction, is specifically contemplated.

The resultant masked 1-halo-4-aminoestradiol according to the Formula V is then either isolated as an end product, or treated as an intermediate, without interim isolation. The intermediate is deaminated by the process described in U.S. application Ser. No. 619,203 (to Hylarides, et al, filed on June 11, 1984 and entitled: DEAMINATION OF AROMATIC AMINES. Deamination and demethylation of the resultant 3-methoxy derivatives of the Formula V are carried out by known procedures to give 1-haloestradiols of the Formula VI. In an exemplary procedure, deamination of 4-amino-1-bromo-3-methoxyestradiol is accomplished by formation and removal of the corresponding diazonium salt, followed by demethylation of the product (BBr3 in anhydrous methylene chloride) is exemplified. The deamination procedure is broadly applicable to compounds according to the present invention. In general, equimolar quantities of reactants (in all steps a–e) will suffice.

While the description of the invention has particularly been directed to simple derivatives of estrone of the Formula IV, or more complicated estrone derivatives of the Formula IVa, the process of the invention is generally applicable to steriod, particularly estrogen compounds, of the type including a phenolic moiety of the formula:

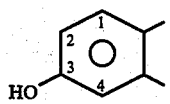

wherein substantially exclusive substitution of halogen in the 1-position is desired, with good yields (50% to 60% of theoretical are contemplated). A further elaboration of the process of the present invention is found in the Hylarides, et al manuscript, "Synthesis of 1-Bromoestradiol", *J. Org. Chem.*: (1984) in press.

The following Examples illustrate the practice of the invention:

EXAMPLE I

A. Preparation of 4-aminoestrone-3-methylether

According to prior art methods (see, e.g., Utne op. cit.).

B. Preparation of 4-aminoestradiol-3-methylether

By reduction of 4-aminoestrone-3-methylether from Example IA, supra.

To an ice-cold solution of 4-aminoestrone-3-methylether in 30 ml freshly distilled THF was added 2.64 g (10.4 mmol) of LiAl(OtBu)3H. The resultant reaction mixture was allowed to warm to room temperature and then stirred for an additional 30 minutes. The mixture was then cooled to 0° C. and hydrolyzed by slow addition of water (10 ml), 40% KOH (10 ml), and 1 gm Na tartrate. Ethyl ether (40 ml) was added and the organic phase was washed with water and dried over anhydrous MgSO4. Removal of the solvents under reduced pressure gave 0.74 g (95% of theoretical) yield of 4-amino-3-methoxyestradiol recrystallized from methanol (m.p. 175°–177° C.).

C. Preparation of 1-bromoestradiol-3-methylether

By bromination and deamination of 4-aminoestradiol-3-methylether from Example 1B, supra.

A mixture of 89.1 mg. (0.865 mmol) NaBr and 115.1 mg. (0.865 mmol) of NCS in 26 ml of 1:1 dioxane/acetic acid was allowed to stir at 25° C. for 10 minutes. (Solvent systems other than dioxane/acetic acid, such as methanol, may be employed, as known in the art; however, the disclosed system permits a "one pot" bromination and deamination). After the addition of 0.26 g (0.865 mmol) of 4-aminoestradiol-3-methylether (as a solid) the reaction mixture was stirred for an additional one hour to yield 1-bromo-4-aminoestradiol-3-methylether. The pale grey solution was then cooled to 0° C. and 10.59 ml of 0.67M HCl was added, followed by 0.26 ml of 3% $H_2O_2$. Finally, a solution of 60 mg (0.87 mmol) of NaNO2, (comprising a slight excess) in 4.2 ml H2O was added slowly. The resultant pale yellow solution was allowed to stir at 0° C. for 20 minutes. The reaction mixture was poured into 30 ml 10% KOH and extracted with ethyl acetate. The organic phase was then washed with water, dried over MgSO4, and the solvents removed under reduced pressure to afford 0.21 g of crude product. The crude product was purified by chromatography (MPLC system) using silica gel and 15% ethyl acetate-toluene: 150 mg (50% yield) of 1-bromoestradiol-3-methylether as a while solid was obtained, mp.=118.5° to 120° C.

If required, the 1-bromo-4-aminoestradiol-3-methylether intermediate is stable and can be isolated by the following steps:

The pale gray reaction mixture solution was poured into 60 ml 5% NaOH. The resulting mixture was extracted with Et acetate. The organic phase was washed with 5% NaOH and with H2O. After drying over anhydrous MgSO4, the solvents were removed under reduced pressure. The crude material was purified by MPLC using 15% ethyl acetate-toluene. After isolation, 0.19 g (58% yield) of 1-bromo-4-aminoestradiol-3-methylether as a pale yellow solid was obtained, mp.=55°–60° C.

D. Preparation of 1-bromoestradiol

By demethylation of 1-bromoestradiol-3-methylether from Example IC, supra.

A solution of 1-bromoestradiol-3-methylether (116 mg, 0.32 mmoles), and 5 ml CH2Cl2 was cooled to 0° C. under N2, followed by dropwise addition of 0.64 ml (0.64 mmoles) of 1M BBr3 in CH2Cl2. The cold bath was removed and the mixture was allowed to stir at 25° C. for 1.25 hours. After the addition of 10 ml of saturated NaCl solution and 20 ml Et-acetate the organic phase was isolated, washed with water and dried over anhydrous MgSO4. Removal of the solvent under reduced pressure gave 100 mg. crude red material, which was chromatographed by MPLC with 15% ethyl acetate-toluene as eluant. Collection of the appropriate fractions followed by removal of solvents gave 50 mg (44% yield) of a white crystalline solid, mp. 239°–241° C. (1-bromoestradiol). The analytical sample was obtained by recrystallization from methanol-water, mp.=242°-244° C.

EXAMPLE II

The procedure of Example I (B-D) is followed except employing 4-amino-17-ethynylestradiol-3-methylether as starting material. The final product is 1-bromo-17β-ethynylestradiol.

What is claimed is:

1. Estradiol or a derivative thereof having a 1-halo substituent.

2. The compound of claim 1, wherein halo is fluoro, chloro, or bromo, or radiohalo thereof.

3. The compound of claim 2, wherein halo is $^{77}$Br or $^{82}$Br.

4. A method for halogenating an estrogen containing an aromatic ring of the formula:

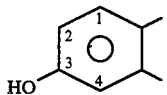

at the 1-position thereof comprising
   (a) masking the 3-hydroxyl group of the aromatic ring
   (b) aminating the aromatic ring at the 4-position thereof; and
   (c) halogenating the aromatic ring by electrophilic substitution of a halogen atom at the 1-position thereof.

5. The method of claim 4, wherein the estrogen containing the aromatic ring is estrone.

6. The method of claim 4, wherein the halogenated aromatic ring is subsequently deaminated, and the 3-hydroxyl group is unmasked.

7. The method of claim 4, wherein the 3-hydroxyl group of the aromatic ring is masked by etherification.

8. The method of claim 7, wherein the etherification product is an ring of the formula

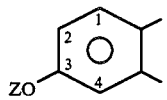

wherein Z is $C_1$-$C_4$-alkyl.

9. The method of claim 8, wherein Z is methyl.

10. The method of claim 5, wherein the estrone is reduced after the aromatic ring is aminated and the 3-hydroxyl group masked, to form a masked 4-aminoestradiol.

11. The method of claim 10, wherein the masked, aminated estrone is reduced with LiAl(OtBu)$_3$H.

12. The method of claim 4, wherein the halogenation proceeds in a dioxane/acetic acid solvent system.

13. The method of claim 10, wherein the 3-hydroxyl group is masked by etherification.

14. The method of claim 13, wherein the masked 4-aminoestradiol is halogenated in the 1-position by electrophilic substitution of fluoro, bromo, chloro, or a radioisotope thereof, and the resultant masked 1-halo-4-aminoestradiol is deaminated and unmasked to form the corresponding 1-haloestradiol.

15. The method of claim 14, wherein the 3-hydroxyl group is masked by etherification to a ($C_1$-$C_4$-alkyl) ether group.

16. The method of claim 4, wherein the electrophilic substituent is prepared from a halide salt and N-chlorosuccinimide.

17. The method of claim 14, wherein the electrophilic substituent ia prepared from a halide salt and N-chlorosuccinimide.

18. The method of claim 14, wherein the 4-aminoestradiol is deaminated by formation and removal of the corresponding diazonium salt.

19. The method of claim 15, wherein the $C_1$-$C_4$-alkyl mask is removed by dealkylation with BBr$_3$.

20. The method of claim 14, wherein the 1-haloestradiol is 1-bromoestradiol.

21. A compound according to claim 1 of the formula

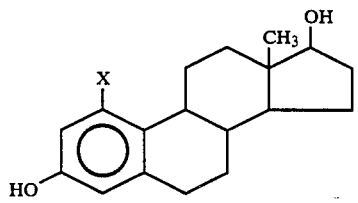

wherein X is halo, or radiohalo.

22. A compound according to claim 21, wherein X is radiohalo.

23. A compound according to claim 1 of the formula

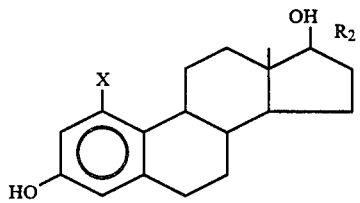

wherein $R_2$ is alkyl, alkenyl, or alkynyl and X is halo or radiohalo.

24. A compound according to claim 23, wherein $R_2$ is ethynyl.

25. A compound according to claim 23, wherein X is bromo and $R_2$ is ethynyl.

* * * * *